United States Patent
Sharma et al.

(10) Patent No.: US 12,254,408 B2
(45) Date of Patent: Mar. 18, 2025

(54) PATTERNED SUBSTRATE FOR USE IN IMAGE-BASED CLASSIFICATION OF ROCK CUTTINGS

(71) Applicant: Schlumberger Technology Corporation, Sugar Land, TX (US)

(72) Inventors: Richa Sharma, Cambridge, MA (US); Quincy K. Elias, Hyde Park, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 411 days.

(21) Appl. No.: 17/756,393

(22) PCT Filed: Dec. 15, 2020

(86) PCT No.: PCT/US2020/065140
§ 371 (c)(1),
(2) Date: May 24, 2022

(87) PCT Pub. No.: WO2021/126866
PCT Pub. Date: Jun. 24, 2021

(65) Prior Publication Data
US 2023/0030441 A1     Feb. 2, 2023

Related U.S. Application Data (60) Provisional application No. 62/948,504, filed on Dec. 16, 2019.

(51) Int. Cl.
*G01N 33/24* (2006.01)
*G06N 3/08* (2023.01)
(Continued)

(52) U.S. Cl.
CPC ............... *G06N 3/08* (2013.01); *G01N 33/24* (2013.01); *G06T 7/60* (2013.01); *G06V 10/22* (2022.01); *G06T 2207/30181* (2013.01)

(58) Field of Classification Search
CPC .......... G06N 3/08; G06N 3/045; G06V 10/22; G06V 10/764; G06V 10/44; G06V 10/10;
(Continued)

(56) References Cited

U.S. PATENT DOCUMENTS 5,777,244 A * 7/1998 Kumagai ............. G01N 21/951
73/865.8
2013/0094716 A1* 4/2013 Carpio ..................... G06T 7/38
382/109
(Continued)

FOREIGN PATENT DOCUMENTS

CA        2734613 A1 *  2/2010   ......... G05D 23/1905
JP      2013190523 A     9/2013
WO  WO-2019117857 A1 *  6/2019   ............. G01B 21/20

OTHER PUBLICATIONS

International Search Report and Written Opinion issued in the PCT Application PCT/US2020/065140, dated Apr. 15, 2021 (9 pages).
(Continued)

*Primary Examiner* — Jeffrey P Aiello
(74) *Attorney, Agent, or Firm* — Jeffrey D. Frantz (57) ABSTRACT

A method of producing an image of at least one rock cutting. The method can include forming or obtaining a substrate having a patterned top surface. The method can also include using the patterned top surface of the substrate to support at least one rock cutting, controlling an image acquisition system to acquire at least one image of the rock cutting for storage and subsequent image processing.

12 Claims, 8 Drawing Sheets

(51) Int. Cl.
*G06T 5/00* (2024.01)
*G06T 7/60* (2017.01)
*G06V 10/22* (2022.01)

(58) Field of Classification Search
CPC ........ G06V 20/10; G06V 20/64; G06F 18/24;
G06F 18/22; G06T 2207/30181; G06T
7/60; G01N 33/24; G01N 21/8851; G01N
21/31; G01N 15/1433; G01N 2223/616;
G01N 23/2251
USPC ............... 73/152.05, 38; 345/419; 356/30;
382/109, 154, 162, 181, 190; 702/2, 16,
702/8, 27, 35, 9, 11; 703/10
See application file for complete search history.

(56) References Cited

U.S. PATENT DOCUMENTS

| | | | |
|---|---|---|---|
| 2018/0147658 A1* | 5/2018 | Shapiro | B23K 26/0853 |
| 2019/0033232 A1* | 1/2019 | Ahn | H01L 22/12 |
| 2021/0042906 A1* | 2/2021 | Bean | G06V 10/764 |

OTHER PUBLICATIONS

International Preliminary Report on Patentability issued in the PCT Application PCT/US2020/065140 dated Jun. 30, 2022, 6 pages.

* cited by examiner

Figure 2A:
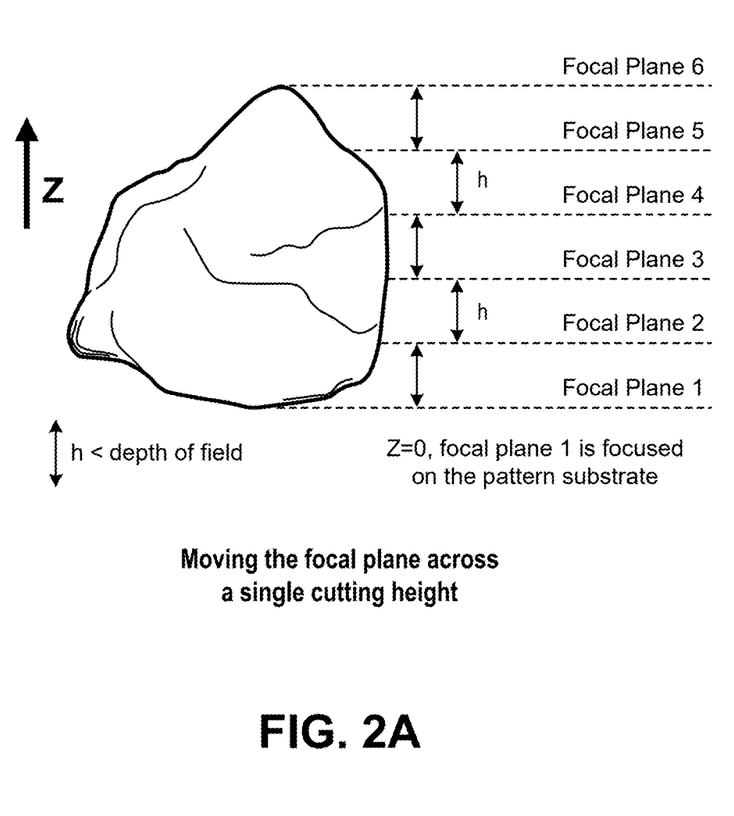

Capturing images (1 through 6) while moving the plane of focus over a subject (cuttings) in incremental steps as represented in figure 2A. As shown in the zoomed in picture on right, Image 1 sets the first plane of stacking by focusing on the patterned substrate or the zero height (z) level of the cutting. Image 1 is z = 0 of the cutting.

Uniform (plain or non patterned) substrate reflects light at identical angles, potentially causing significant glare.

FIG. 4A

FIG. 4B

Patterned substrate fabricated by laser etching of 4A. Different planes and angles of the micron size features on a patterned substrate lead to light being reflected at different angles. The scattered light leads to much more favorable "diffuse reflection".

Patterned substrate as background. The shadow of the cutting is diffused.

FIG. 5B

Plain (flat or non-patterned) substrate. The shadow of the cutting is sharp and distinct.

PATTERNED SUBSTRATE FOR USE IN IMAGE-BASED CLASSIFICATION OF ROCK CUTTINGS

This application is a National Stage Entry of International Application No. PCT/US2020/065140 filed Dec. 15, 2020, which claims benefit of U.S. Provisional Patent Application Ser. No. 62/948,504 filed on Dec. 16, 2019, which is incorporated herein by reference in its entirety.

The present disclosure relates to methods and systems that acquire images of rock cuttings and process the images for automated classification of the rock cuttings.

The present disclosure describes new methods and systems that employ a substrate that supports rock cuttings during image acquisition and facilitates the processing of such images for automated classification of the rock cuttings. In embodiments, the substrate can include patterns (or a pattern of features) engraved or otherwise formed in a planar surface of material. The patterns can be formed by laser etching, printing or other deposition of a monolayer of close-packed nanoparticles or other suitable method. In embodiments, dithering algorithms (such as Stucki dithering, Floyd-Steinberg dithering and Jarvis dithering) can be used to define the patterns formed in the substrate. Furthermore, in embodiments, the patterned substrate can be blue in color in order to provide a blue background for the rock cuttings. The blue background is advantageous because rock cuttings of interest tend to have dissimilar color.

The methods and systems of the subject disclosure are especially suitable for automated image-based classification of rock cuttings, such as texture-based deep learning classification of rock cuttings. Extensive experimentation has shown that deep learning algorithms perform better if the training image samples have high magnification and sharp focus. Using the macro mode of image capture can achieve these properties. However, in practice, acquiring images of the rock cuttings with all the cuttings in focus is extremely difficult owing to the fact that macro photography has a shallow depth of field, and typical cutting sizes are a few (2-5) times larger than the depth of field.

In order to address this problem, focus stacking (also referred to as focal plane merging) can be used to obtain sharp images of rock cutting mixtures. The proposed method employs the patterned substrate in conjunction with focus stacking and provides for improved results. The key advantages can be summarized as follows.

Systematic and reproduceable approach to automating focus stacking

Figure 2B:
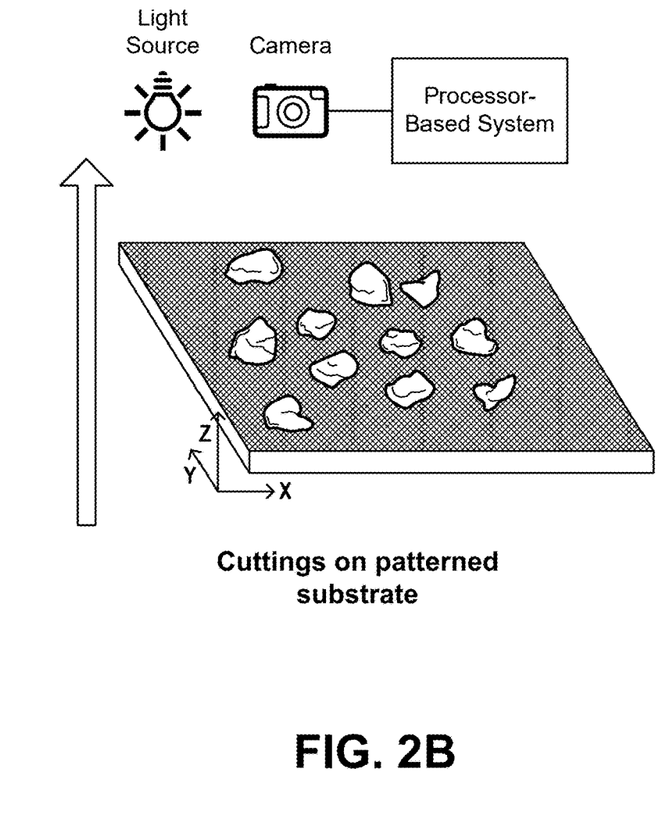

Focus stacking can be used to capture a sharp image of rock cuttings with all the rock cuttings, including rock texture details, in focus. Focus stacking involves moving the plane of focus of an image acquisition system (e.g., a camera with fixed or variable focus lens) over the subject rock cuttings in incremental steps. During each small movement, the image acquisition system is controlled to take an image or photo, working from top to bottom or reverse. The image acquisition system can include a camera (with fixed or variable focus lens) and a light source as shown in FIG. 2B. The resulting sequence of images is then processed by aligning and merging the images in post-production. Such post-production image processing can be carried out by a processor-based system as shown in FIG. 2B. The proposed methods and systems of the present disclosure adapts the focus stacking workflow by configuring one or more focus settings of the image acquisition system such that the plane of focus for the first acquired image is at or near the plane of the top surface of the substrate, which corresponds to the zero height (z) level of the rock cuttings. At such focus setting(s), the image acquisition system is focused on the patterns formed in the patterned substrate. Such focus setting(s) can be determined manually or possibly by automatic methods such as autofocus methods. The patterned features formed in the top surface of the substrate (which can be microns in size or less) enable this fine focusing. Once these focus setting(s) have been determined, such focus setting(s) can be registered or stored in electronic form (for example, in computer memory) and then accessed and used for follow-on image acquisition and focus stacking. This eliminates the need to determine these focus setting(s) of the image acquisition system for imaging each new sample.

Reduced reflection and glare from the substrate

One of the limitations of a uniform (plain) substrate is that it reflects light at identical angles, potentially causing significant glare. On the other hand, the different planes and angles of the features created on the top surface of the patterned substrate can lead to light being reflected at a different angles. The scattered light provides much more favorable "diffuse reflection."

Diffused (or less sharp) shadow of the target object

The proposed methods and systems of the present disclosure can aid in eliminating the need to perform shadow detection and removal as a costly image pre-processing step. It is important to note that a sharp or crisp shadow can compromise the performances of even the most advanced deep learning models. While separating the shadow from a familiar object in an image is not difficult for a human brain, it remains to be a challenging (and ill-posed) problem for computer vision. One can always propose and train a novel deep convolutional encoder-decoder model to remove the objectionable shadows by learning a map between image pairs with and without shadow. However, this step can be quite costly in terms of time budget and human effort required to train this model. In contrast, diffusing the sharp shadows makes our imaging technique robust to begin with, eliminating the need of identifying the shadow of cuttings. This is a significant advantage because edge detection is not the end goal in the first place. Instead, more effort can be devoted to the design of deep learning automated classification algorithms.

To summarize, the methods and systems of the present disclosure can positively impact the whole data pipeline of automated classification of rock cuttings, including better focus stacking, no need for shadow detection, and better performance of deep learning methods. Such methods and systems are particularly advantageous for automated image-based classification of heterogenous mixtures of rock cuttings.

Figure 1:
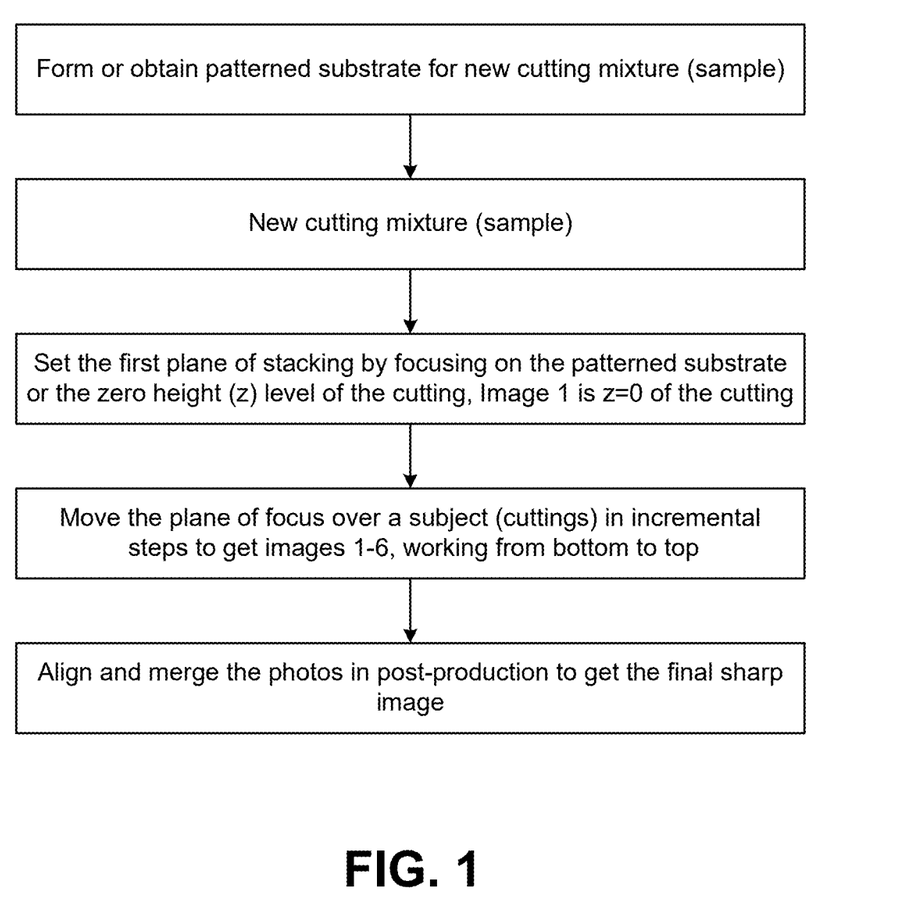

FIG. 1 is a flowchart that illustrates an exemplary workflow for automating image acquisition and focus stacking to produce a sharpened image of rocking cuttings supported on a patterned substrate. Note that the sharpened image of the rock cuttings can be used as training data or observation data that is input for automated image-based classification of rock cuttings, such as texture-based deep learning classification of rock cuttings.

FIG. 2A is a schematic diagram of the focus stacking operation which moves the focal plane of the image acquisition operations across the height of a single rock cutting. Note that the first focal plane can be set by focusing the image acquisition system on the plane of the top surface of the patterned substrate, which focuses the first image on the patterned features of the substrate (which can be microns in size or less).

FIG. 2B is a schematic diagram of rock cuttings supported on a patterned substrate together with an image acquisition system for acquiring images or photos of the rock cuttings supported on the patterned substrate. The image acquisition system can include a camera (with fixed or variable focus lens) and a light source as shown. Note that the patterns are formed on the top surface of the substrate, and the patterned top surface of the substrate is used to support the rock cuttings for image acquisition with focal plane stacking. The focal plane stacking can be carried out by a processor-based system that is operably coupled to the camera as shown in FIG. 2B.

Figure 3:
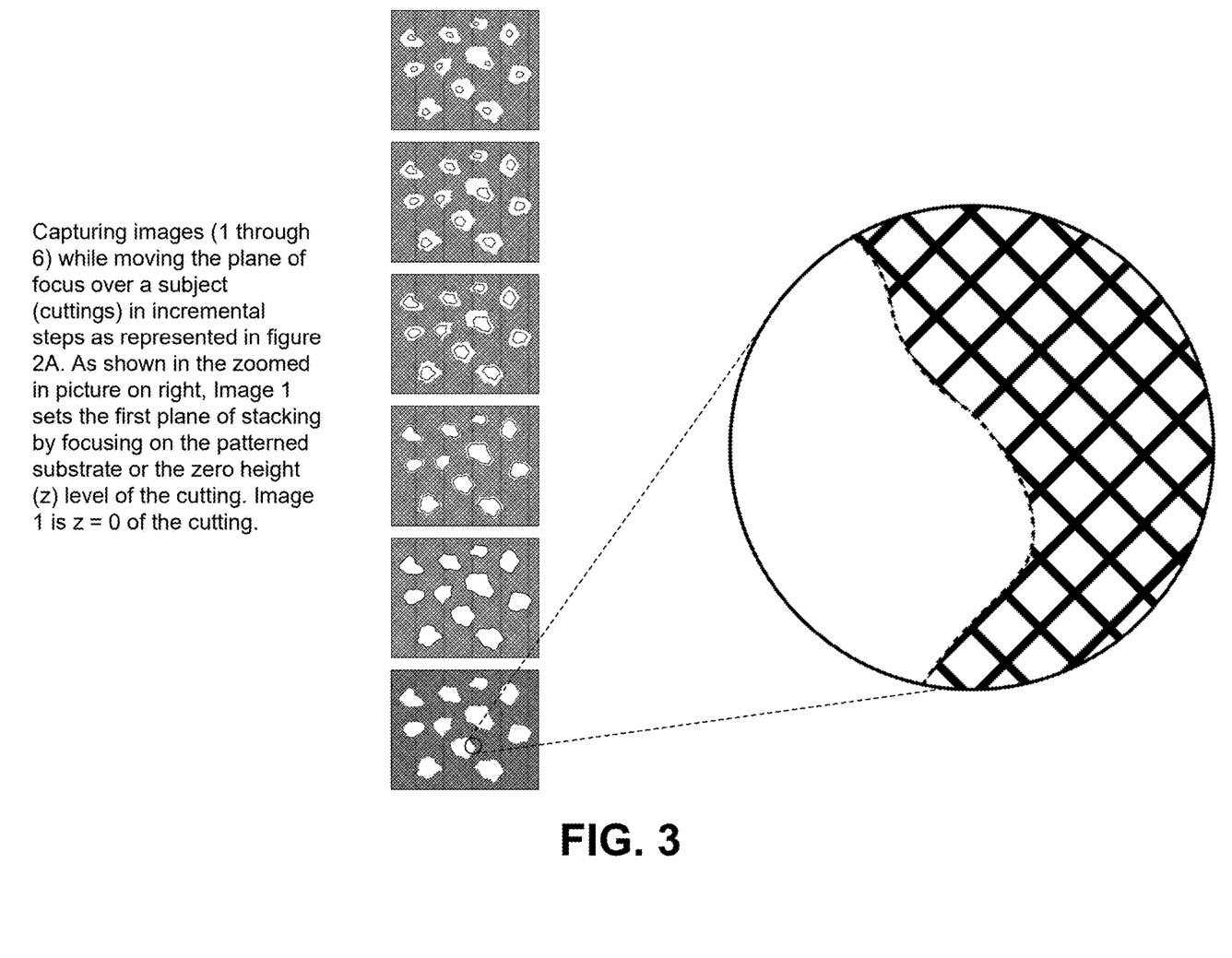

FIG. 3 depicts a sequence of six (6) images that are captured while moving the plane of focus over a sample of rock cuttings supported on a patterned substrate. The plane of focus is moved from the bottom to the top of the rock cuttings in incremental steps as represented in FIG. 2A. As shown in the zoomed picture on the right hand side of FIG. 3, image 1 sets the first plane of stacking by focusing on the patterned substrate. The zero height (z-0) of the cuttings is defined by focusing on the patterns formed in the top surface of the substrate. Image 1 in FIG. 3 corresponds to the focal plane 1 in FIG. 2A. Similarly other images in FIG. 3 correspond to their respective focal planes in FIG. 2A.

Figure 4A:
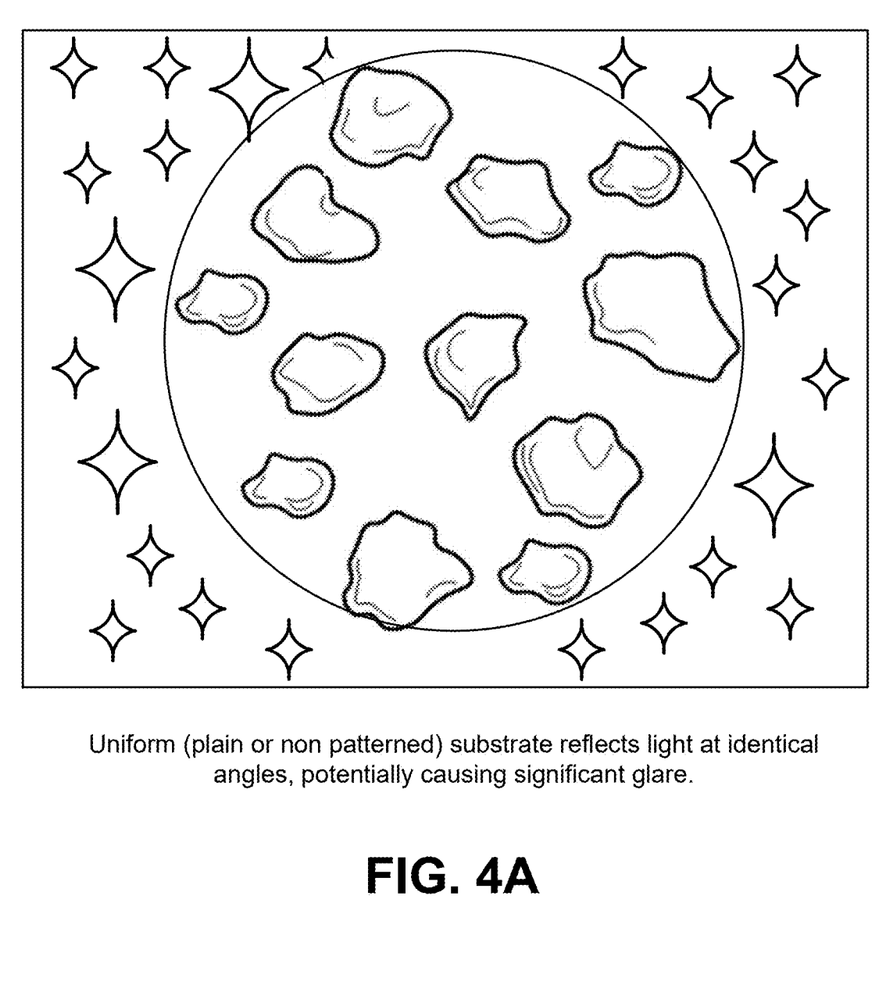
Figure 4B:
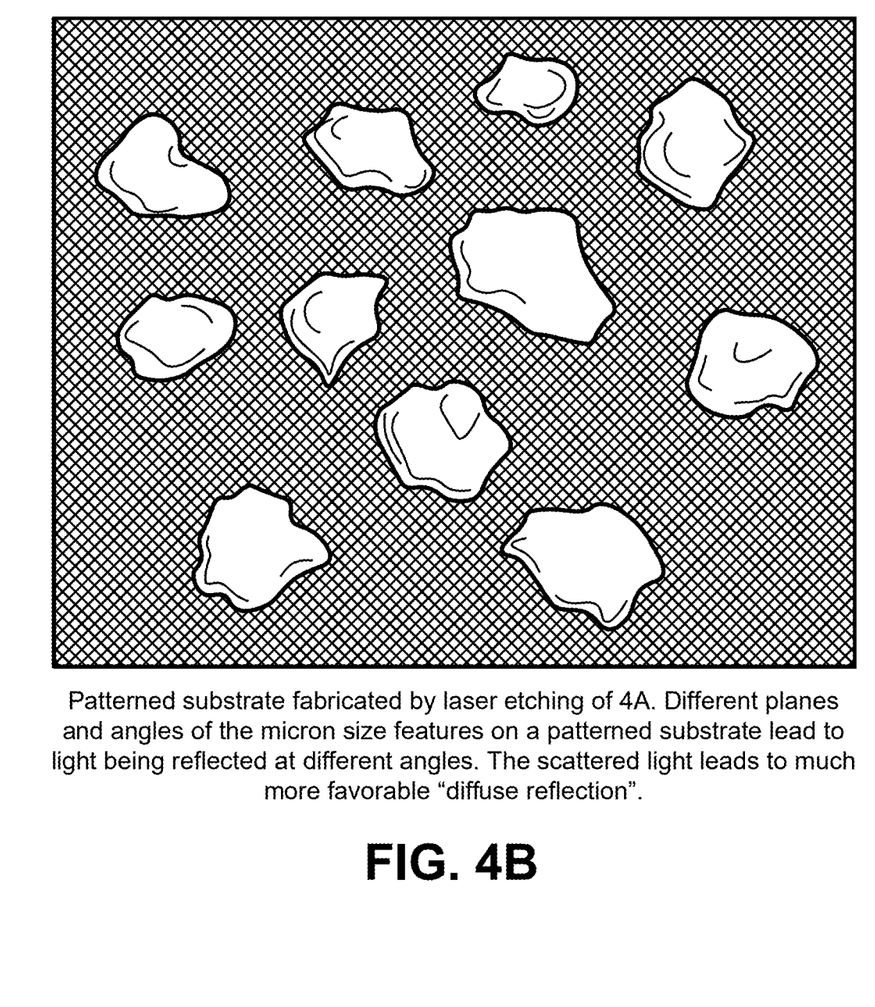

FIG. 4A is an image of rock cuttings supported on a uniform (plain or non-patterned) substrate. Note that the uniform substrate reflects light at identical angles, potentially causing significant glare. FIG. 4B is an image of rock cuttings supported on a patterned substrate fabricated by laser etching. Note that the different planes and angles of the micron sized features formed on the top surface of the patterned substrate lead to light being reflected at different angles. The scattered light leads to much more favorable "diffuse reflection". In this manner, the patterned substrate leads to reduced reflection and glare from the substrate when acquiring the image of rock cuttings supported on the patterned substrate.

Figure 5A:
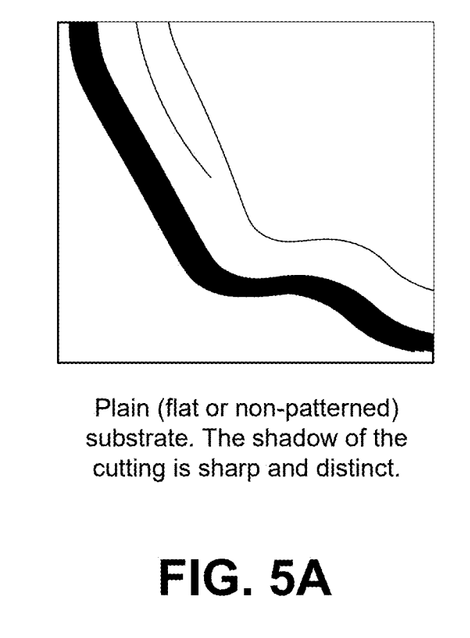
Figure 5B:
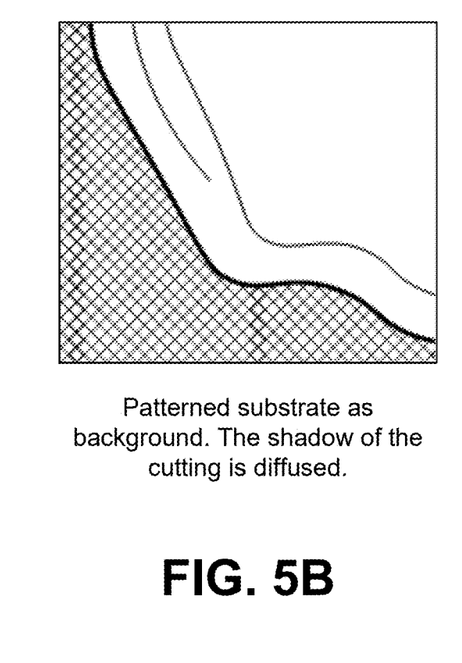

FIG. 5A is an image of a rock cutting supported on a uniform (plain or non-patterned) substrate. Note that the shadow of the rock cutting is sharp and distinct. FIG. 5B is an image of a rock cutting supported on a patterned substrate fabricated by laser etching. Note that the shadow of the rock cutting is diffused. In this manner, the patterned substrate is effective in producing a diffused (or less sharp) shadow of the target rock cuttings.

Figure 6A:
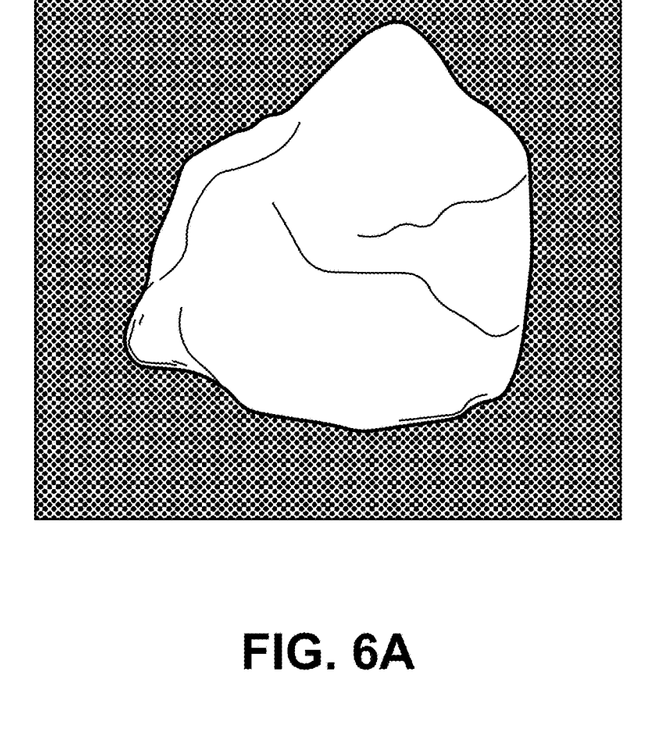
Figure 6B:
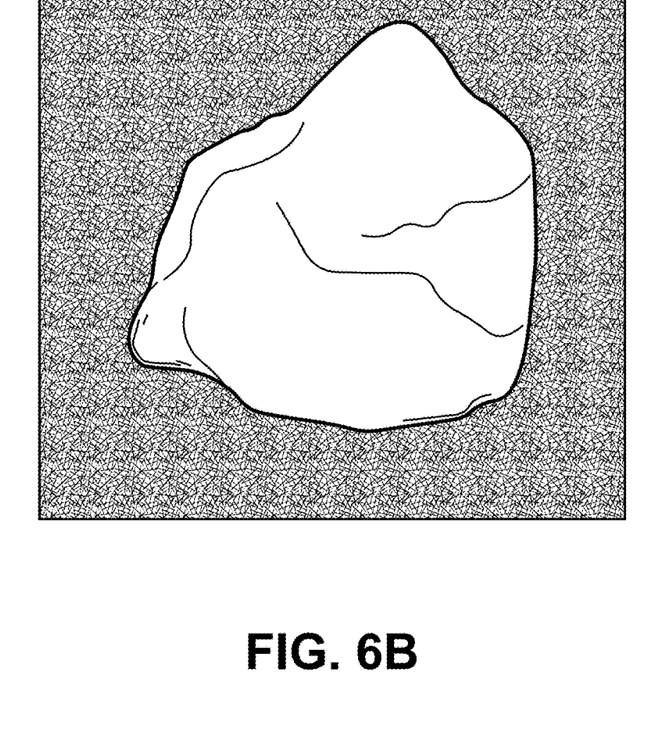

FIGS. 6A and 6B are images of rock cuttings supported on patterned substrates that have different micro-patterns formed in the top surfaces of the substrates.

Figure 7:
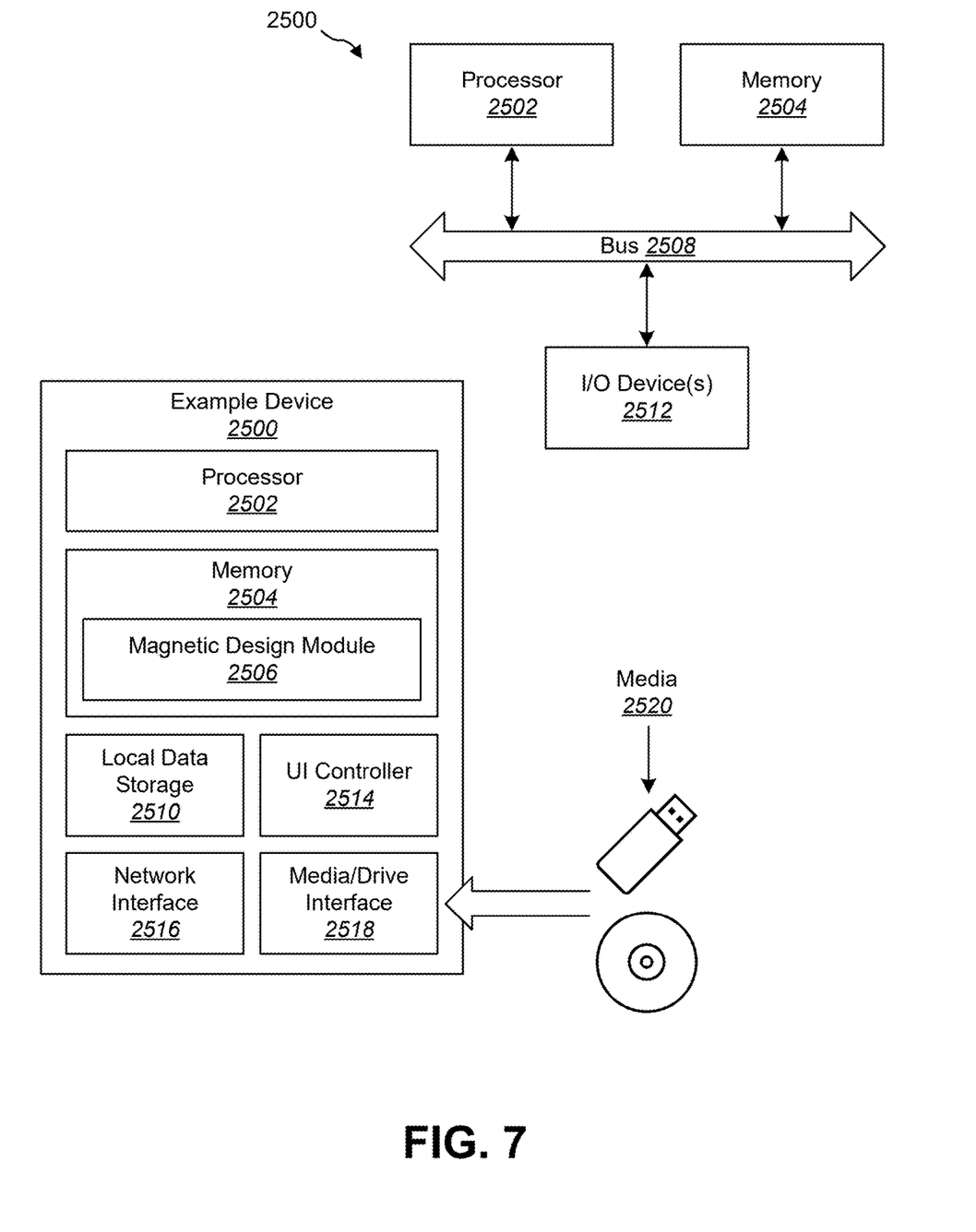

FIG. 7 illustrates an example device 2500, with a processor 2502 and memory 2504 that can be configured to implement various embodiments of the methods and systems for image acquisition using focal plane stacking as well as automated image-based classification of rock cuttings (such as texture-based deep learning classification of rock cutting) as discussed in this disclosure. Memory 2504 can also host one or more databases and can include one or more forms of volatile data storage media such as random-access memory (RAM), and/or one or more forms of nonvolatile storage media (such as read-only memory (ROM), flash memory, and so forth).

Device 2500 is one example of a computing device or programmable device and is not intended to suggest any limitation as to a scope of use or functionality of device 2500 and/or its possible architectures. For example, device 2500 can comprise one or more computing devices, programmable logic controllers (PLCs), etc.

Further, device 2500 should not be interpreted as having any dependency relating to one or a combination of components illustrated in device 2500. For example, device 2500 may include one or more of computers, such as a laptop computer, a desktop computer, a mainframe computer, etc., or any combination or accumulation thereof.

Device 2500 can also include a bus 2508 configured to allow various components and devices, such as processors 2502, memory 2504, and local data storage 2510, among other components, to communicate with each other.

Bus 2508 can include one or more of any of several types of bus structures, including a memory bus or memory controller, a peripheral bus, an accelerated graphics port, and a processor or local bus using any of a variety of bus architectures. Bus 2508 can also include wired and/or wireless buses.

Local data storage 2510 can include fixed media (e.g., RAM, ROM, a fixed hard drive, etc.) as well as removable media (e.g., a flash memory drive, a removable hard drive, optical disks, magnetic disks, and so forth).

One or more input/output (I/O) device(s) 2512 may also communicate via a user interface (UI) controller 2514, which may connect with I/O device(s) 2512 either directly or through bus 2508.

In one possible implementation, a network interface 2516 may communicate outside of device 2500 via a connected network.

A media drive/interface 2518 can accept removable tangible media 2520, such as flash drives, optical disks, removable hard drives, software products, etc. In one possible implementation, logic, computing instructions, and/or software programs comprising elements of a module 2506 may reside on removable media 2520 readable by media drive/interface 2518. Various processes of the present disclosure or parts thereof can be implemented by instructions and/or software programs that are elements of module 2506. Such instructions and/or software programs may reside on removable media 2520 readable by media drive/interface 2518 as is well known in the computing arts.

In one possible embodiment, I/O device(s) 2512 can allow a user (such as a human annotator) to enter commands and information to device 2500, and also allow information to be presented to the user and/or other components or devices. Examples of input device(s) include, for example, sensors, a keyboard, a cursor control device (e.g., a mouse), a microphone, a scanner, and any other input devices known in the art. Examples of output devices include a display device (e.g., a monitor or projector), speakers, a printer, a network card, and so on.

Various processes of the present disclosure may be described herein in the general context of software or program modules, or the techniques and modules may be implemented in pure computing hardware. Software generally includes routines, programs, objects, components, data structures, and so forth that perform particular tasks or implement particular abstract data types. An implementation of these modules and techniques may be stored on or transmitted across some form of tangible computer-readable media. Computer-readable media can be any available data storage medium or media that is tangible and can be accessed by a computing device. Computer readable media may thus comprise computer storage media. "Computer storage media" designates tangible media, and includes volatile and non-volatile, removable and non-removable tangible media implemented for storage of information such as computer readable instructions, data structures, program modules, or other data. Computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible medium which can be used to store the desired information, and which can be accessed by a computer. Some of the methods and processes described above, can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general-purpose computer) for executing any of the methods and processes described above.

Some of the methods and processes described above, can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASICS)), and/or programmable logic devices (e.g., Field Programmable Gate Arrays (FPGAs)). Any of the methods and processes described above can be implemented using such logic devices.

In one or more embodiments, a system for producing an image of at least one rock cutting can include a substrate having a patterned top surface; and an image acquisition system configured to acquire at least one image of a rock cutting while using the patterned top surface of the substrate to support the rock cutting.

In one or more embodiments, the image acquisition system can include a camera with a fixed or variable focus lens and a light source.

In one or more embodiments, the image acquisition system can be configured to acquire a plurality of images of the rock cutting at different focus settings corresponding to different height levels across a height of the rock cutting, wherein at least one of the focus settings corresponds to the plane of the top surface of the patterned substrate.

In one or more embodiments, the focus setting corresponding to the plane of the top surface of the patterned substrate focuses the image acquisition system on patterns formed in the patterned substrate.

In one or more embodiments, the focus setting corresponding to the plane of the top surface of the patterned substrate is determined manually or by automatic methods.

In one or more embodiments, a system for producing an image of at least one rock cutting can include a substrate having a patterned top surface; and an image acquisition system configured to acquire at least one image of a rock cutting while using the patterned top surface of the substrate to support the rock cutting, and a processor configured to register or store in electronic form the focus setting corresponding to the plane of the top surface of the patterned substrate for access and use in imaging at least one additional sample of rock cuttings.

In one or more embodiments, a system for producing an image of at least one rock cutting can include a substrate having a patterned top surface; and an image acquisition system configured to acquire at least one image of a rock cutting while using the patterned top surface of the substrate to support the rock cutting, and a processor configured to align and merge the plurality of images to produce a sharpened image of the rock cutting.

In one or more embodiments, the sharpened image of the rock cutting is used as input for automated image-based classification of rock cuttings (such as texture-based deep learning classification of rock cuttings).

In one or more embodiments, the sharpened image of the rock cutting is used as training data or observation data that is input for automated image-based classification of rock cuttings.

a system for producing an image of at least one rock cutting can include a substrate having a patterned top surface; and an image acquisition system configured to acquire at least one image of a rock cutting while using the patterned top surface of the substrate to support the rock cutting, wherein the patterned top surface of the substrate is formed by laser cutting, or by printing or other deposition of nanoparticles.

In one or more embodiments, a system for producing an image of at least one rock cutting can include a substrate having a patterned top surface; and an image acquisition system configured to acquire at least one image of a rock cutting while using the patterned top surface of the substrate to support the rock cutting, wherein the patterned top surface of the substrate is defined by a dithering algorithm (such as Stucki dithering, Floyd-Steinberg dithering, or Jarvis dithering).

In one or more embodiments, a system for producing an image of at least one rock cutting can include a substrate having a patterned top surface; and an image acquisition system configured to acquire at least one image of a rock cutting while using the patterned top surface of the substrate to support the rock cutting, wherein the patterned top surface of the substrate provides a blue background for the rock cutting.

In one or more embodiments, a system for producing an image of at least one rock cutting can include a substrate having a patterned top surface; and an image acquisition system configured to acquire at least one image of a rock cutting while using the patterned top surface of the substrate to support the rock cutting, wherein the system is configured to produce images of a plurality or mixture of rock cuttings.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

There have been described and illustrated herein several embodiments of methods and systems for producing an image of one or more rock cuttings. While particular embodiments have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as claimed.

What is claimed is:

1. A method for automated classification of rock cuttings, comprising:
    forming a substrate having a patterned top surface;
    while using the patterned top surface of the substrate to support a rock cutting, producing, by an image acquisition system, a sequence of images of the rock cutting using focal plane stacking;
    processing, by one or more computers, the sequence of images by aligning and merging the images to generate a sharpened image of the rock cutting;
    inputting as training data, by the one or more computers, the sharpened image of the rock cutting into an automated texture-based deep learning classifier of rock cuttings; and
    classifying a rock cutting using the automated texture-based deep learning classifier that has been trained using the sharpened image.

2. A method according to claim 1, wherein:
    the image acquisition system comprises a camera with a fixed or variable focus lens and a light source.

3. A method according to claim 1, further comprising:
    controlling the image acquisition system to acquire the sequence of images of the rock cutting, each at different focus settings corresponding to different height levels across a height of the rock cutting, wherein at least one of the focus settings corresponds to the plane of the patterned top surface of the substrate.

4. A method according to claim 3, wherein:
    the focus setting corresponding to the plane of the patterned top surface of the substrate focuses the image acquisition system on patterns formed in the patterned substrate.

5. A method according to claim 3, wherein:
    the focus setting corresponding to the plane of the patterned top surface of the substrate is determined manually or by automatic methods.

6. A method according to claim 3, further comprising:
    registering or storing in electronic form the focus setting corresponding to the plane of the patterned top surface of the substrate for access and use in imaging at least one additional sample of rock cuttings.

7. A method according to claim 1, wherein:
    the patterned top surface of the substrate is formed by laser cutting, or by printing or other deposition of nanoparticles.

8. A method according to claim 1, wherein:
    the patterned top surface of the substrate is defined by a dithering algorithm.

9. A method according to claim 1, wherein:
    the patterned top surface provides a blue background for the rock cutting.

10. A method according to claim 1, which is configured to produce an image of a plurality or mixture of rock cuttings.

11. A method according to claim 8, wherein:
    the dithering algorithm is a Stucki dithering, a Floyd-Steinberg dithering, or a Jarvis dithering.

12. A system for producing an image of at least one rock cutting, comprising:
    a substrate having a patterned top surface and configured to support a rock cutting; and
    an image acquisition system configured to acquire a sequence of images of the rock cutting using focal plane stacking while the rock cutting is supported on the patterned top surface of the substrate.

* * * * *